US008318192B2

(12) United States Patent
Boyan et al.

(10) Patent No.: US 8,318,192 B2
(45) Date of Patent: *Nov. 27, 2012

(54) METHOD OF MAKING LOAD BEARING HYDROGEL IMPLANTS

(75) Inventors: Barbara D. Boyan, Atlanta, GA (US); Robert E. Guldberg, Marietta, GA (US); Stephen J. Kennedy, Atlanta, GA (US); David N. Ku, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 915 days.

This patent is subject to a terminal disclaimer.

(21) Appl. No.: 12/273,450

(22) Filed: Nov. 18, 2008

(65) Prior Publication Data

US 2009/0263446 A1    Oct. 22, 2009

Related U.S. Application Data

(63) Continuation of application No. 11/053,409, filed on Feb. 7, 2005, now Pat. No. 7,910,124.

(60) Provisional application No. 60/542,389, filed on Feb. 6, 2004.

(51) Int. Cl.
*A61F 2/02* (2006.01)

(52) U.S. Cl. ........................................................ 424/423

(58) Field of Classification Search ........................ None
See application file for complete search history.

(56) References Cited

U.S. PATENT DOCUMENTS

| | | | |
|---|---|---|---|
| 3,276,996 A | 10/1966 | Lazare | |
| 3,663,470 A | 5/1972 | Nishimura et al. | |
| 3,673,612 A | 7/1972 | Merrill et al. | |
| 3,849,238 A | 11/1974 | Gould et al. | |
| 3,859,421 A | 1/1975 | Hucke | |
| 4,083,906 A | 4/1978 | Schindler et al. | |
| 4,205,400 A | 6/1980 | Shen et al. | |
| 4,351,069 A | 9/1982 | Ballintyn et al. | |
| 4,472,542 A | 9/1984 | Nambu | |
| 4,517,295 A | 5/1985 | Bracke et al. | |
| 4,524,064 A | 6/1985 | Nambu | |
| 4,609,337 A | 9/1986 | Wichterle et al. | |
| 4,663,358 A | 5/1987 | Hyon et al. | |
| 4,664,857 A | 5/1987 | Nambu | |
| 4,693,939 A | 9/1987 | Ofstead | |
| 4,731,081 A | 3/1988 | Tiffany et al. | |
| 4,734,097 A | 3/1988 | Tanabe et al. | |
| 4,753,761 A | 6/1988 | Suzuki | |

(Continued)

FOREIGN PATENT DOCUMENTS

DE              20218703            3/2003

(Continued)

OTHER PUBLICATIONS

Bray et al., M. Biomed. Mater. Res., 1973, 7, 431-443.

(Continued)

*Primary Examiner* — Carlos Azpuru
(74) *Attorney, Agent, or Firm* — Knobbe, Martens, Olson & Bear, LLP (57) ABSTRACT

Implantable biomaterials, particularly hydrogel substrates with porous surfaces, and methods for enhancing the compatibility of biomaterials with living tissue, and for causing physical attachment between biomaterials and living tissues are provided. Also provided are implants suitable for load-bearing surfaces in hard tissue repair, replacement, or augmentation, and to methods of their use. One embodiment of the invention relates to an implantable spinal disc prosthesis.

12 Claims, 2 Drawing Sheets

U.S. PATENT DOCUMENTS

| | | |
|---|---|---|
| 4,759,766 A | 7/1988 | Buttner-Janz et al. |
| 4,772,284 A | 9/1988 | Jefferies et al. |
| 4,784,990 A | 11/1988 | Nimrod et al. |
| 4,787,905 A | 11/1988 | Loi |
| 4,808,353 A | 2/1989 | Nambu et al. |
| 4,828,493 A | 5/1989 | Nambu et al. |
| 4,851,168 A | 7/1989 | Graiver et al. |
| 4,911,720 A | 3/1990 | Collier |
| 4,916,170 A | 4/1990 | Nambu |
| 4,988,761 A | 1/1991 | Ikada et al. |
| 4,995,882 A | 2/1991 | Destouet et al. |
| 5,047,055 A | 9/1991 | Bao et al. |
| 5,080,674 A | 1/1992 | Jacobs et al. |
| 5,095,037 A | 3/1992 | Iwamitsu et al. |
| 5,106,743 A | 4/1992 | Franzblau et al. |
| 5,106,876 A | 4/1992 | Kawamura |
| 5,108,428 A | 4/1992 | Capecchi et al. |
| 5,108,436 A | 4/1992 | Chu et al. |
| 5,118,667 A | 6/1992 | Adams et al. |
| 5,141,973 A | 8/1992 | Kobayashi et al. |
| 5,171,322 A | 12/1992 | Kenny |
| 5,171,574 A | 12/1992 | Kuberasampath et al. |
| 5,192,326 A | 3/1993 | Bao et al. |
| 5,206,023 A | 4/1993 | Hunziker |
| 5,219,360 A | 6/1993 | Georgiade |
| 5,234,456 A | 8/1993 | Silvestrini |
| 5,244,799 A | 9/1993 | Anderson |
| 5,258,023 A | 11/1993 | Reger |
| 5,258,042 A | 11/1993 | Mehta |
| 5,258,043 A | 11/1993 | Stone |
| 5,260,066 A | 11/1993 | Wood et al. |
| 5,287,857 A | 2/1994 | Mann |
| 5,288,503 A | 2/1994 | Wood et al. |
| 5,290,494 A | 3/1994 | Coombes et al. |
| 5,314,477 A | 5/1994 | Marnay |
| 5,314,478 A | 5/1994 | Oka et al. |
| 5,326,364 A | 7/1994 | Clift, Jr. et al. |
| 5,336,551 A | 8/1994 | Graiver et al. |
| 5,336,767 A | 8/1994 | Della Valle et al. |
| 5,343,877 A | 9/1994 | Park |
| 5,344,459 A | 9/1994 | Swartz |
| 5,346,935 A | 9/1994 | Suzuki et al. |
| 5,397,572 A | 3/1995 | Coombes et al. |
| 5,399,591 A | 3/1995 | Smith et al. |
| 5,401,269 A | 3/1995 | Buttner-Janz et al. |
| 5,409,904 A | 4/1995 | Hecht et al. |
| 5,410,016 A | 4/1995 | Hubbell et al. |
| 5,442,053 A | 8/1995 | Della Valle et al. |
| 5,458,643 A | 10/1995 | Oka et al. |
| 5,458,645 A | 10/1995 | Bertin |
| 5,489,310 A | 2/1996 | Mikhail |
| 5,490,962 A | 2/1996 | Cima et al. |
| 5,492,697 A | 2/1996 | Boyan et al. |
| 5,494,940 A | 2/1996 | Unger et al. |
| 5,502,082 A | 3/1996 | Unger et al. |
| 5,512,475 A | 4/1996 | Naughton et al. |
| 5,522,898 A | 6/1996 | Bao |
| 5,534,028 A | 7/1996 | Bao et al. |
| 5,541,234 A | 7/1996 | Unger et al. |
| 5,545,229 A | 8/1996 | Parsons et al. |
| 5,556,429 A | 9/1996 | Felt |
| 5,556,431 A | 9/1996 | Buttner-Janz |
| 5,578,217 A | 11/1996 | Unger et al. |
| 5,626,861 A | 5/1997 | Laurencin et al. |
| 5,645,592 A | 7/1997 | Nicolais et al. |
| 5,656,450 A | 8/1997 | Boyan et al. |
| 5,658,329 A | 8/1997 | Purkait |
| 5,674,241 A | 10/1997 | Bley et al. |
| 5,674,295 A | 10/1997 | Ray et al. |
| 5,674,296 A | 10/1997 | Bryan et al. |
| 5,688,459 A | 11/1997 | Mao et al. |
| 5,700,289 A | 12/1997 | Breitbart et al. |
| 5,705,780 A | 1/1998 | Bao |
| 5,716,416 A | 2/1998 | Lin |
| 5,750,585 A | 5/1998 | Park et al. |
| 5,766,618 A | 6/1998 | Laurencin et al. |
| 5,769,897 A | 6/1998 | Harle |
| 5,789,464 A | 8/1998 | Muller |
| 5,795,353 A | 8/1998 | Felt |
| 5,824,093 A | 10/1998 | Ray et al. |
| 5,824,094 A | 10/1998 | Serhan et al. |
| 5,844,016 A | 12/1998 | Sawhney et al. |
| 5,847,046 A | 12/1998 | Jiang et al. |
| 5,855,610 A | 1/1999 | Vacanti et al. |
| 5,863,297 A | 1/1999 | Walter et al. |
| 5,863,551 A | 1/1999 | Woerly |
| 5,876,452 A | 3/1999 | Athanasiou et al. |
| 5,876,741 A | 3/1999 | Ron |
| 5,880,216 A | 3/1999 | Tanihara et al. |
| 5,900,245 A | 5/1999 | Sawhney et al. |
| 5,916,585 A | 6/1999 | Cook et al. |
| 5,925,626 A | 7/1999 | Della Valle et al. |
| 5,928,239 A | 7/1999 | Mirza |
| 5,935,129 A | 8/1999 | McDevitt et al. |
| 5,944,754 A | 8/1999 | Vacanti |
| 5,947,844 A | 9/1999 | Shimosaka et al. |
| 5,948,829 A | 9/1999 | Wallajapet et al. |
| 5,957,787 A | 9/1999 | Hwang |
| 5,976,186 A | 11/1999 | Bao et al. |
| 5,981,826 A | 11/1999 | Ku et al. |
| 6,001,352 A | 12/1999 | Boyan et al. |
| 6,027,744 A | 2/2000 | Vacanti et al. |
| 6,060,534 A | 5/2000 | Ronan et al. |
| 6,093,205 A | 7/2000 | McLeod et al. |
| 6,102,954 A | 8/2000 | Albrektsson et al. |
| 6,103,255 A | 8/2000 | Levene et al. |
| 6,132,465 A | 10/2000 | Ray et al. |
| 6,156,067 A | 12/2000 | Bryan et al. |
| 6,171,610 B1 | 1/2001 | Vacanti et al. |
| 6,187,329 B1 | 2/2001 | Agrawal et al. |
| 6,206,927 B1 | 3/2001 | Fell |
| 6,224,630 B1 | 5/2001 | Bao et al. |
| 6,231,605 B1 | 5/2001 | Ku |
| 6,255,359 B1 | 7/2001 | Agrawal et al. |
| 6,264,695 B1 | 7/2001 | Stoy |
| 6,268,405 B1 | 7/2001 | Yao et al. |
| 6,271,278 B1 | 8/2001 | Park et al. |
| 6,280,475 B1 | 8/2001 | Bao et al. |
| 6,337,198 B1 | 1/2002 | Levene et al. |
| 6,340,369 B1 | 1/2002 | Ferree |
| 6,341,952 B2 | 1/2002 | Gaylo et al. |
| 6,344,058 B1 | 2/2002 | Ferree |
| 6,355,699 B1 | 3/2002 | Vyakarnam et al. |
| 6,358,251 B1 | 3/2002 | Mirza |
| 6,371,984 B1 | 4/2002 | Van Dyke et al. |
| 6,376,573 B1 | 4/2002 | White et al. |
| 6,379,962 B1 | 4/2002 | Holy et al. |
| 6,383,519 B1 | 5/2002 | Sapieszko et al. |
| 6,402,784 B1 | 6/2002 | Wardlaw |
| 6,402,785 B1 | 6/2002 | Zdeblick et al. |
| 6,419,704 B1 | 7/2002 | Ferree |
| 6,428,576 B1 | 8/2002 | Haldimann |
| 6,451,059 B1 | 9/2002 | Janas et al. |
| 6,472,210 B1 | 10/2002 | Holy et al. |
| 6,482,234 B1 | 11/2002 | Weber et al. |
| 6,531,523 B1 | 3/2003 | Davankov et al. |
| 6,533,818 B1 | 3/2003 | Weber et al. |
| 6,534,084 B1 | 3/2003 | Vyakarnam et al. |
| 6,558,421 B1 | 5/2003 | Fell et al. |
| 6,602,291 B1 | 8/2003 | Ray et al. |
| 6,607,558 B2 | 8/2003 | Kuras |
| 6,610,094 B2 | 8/2003 | Husson |
| 6,629,997 B2 | 10/2003 | Mansmann |
| 6,645,248 B2 | 11/2003 | Casutt |
| 6,667,049 B2 | 12/2003 | Janas et al. |
| 6,686,437 B2 | 2/2004 | Buchman et al. |
| 6,707,558 B2 | 3/2004 | Bennett |
| 6,710,126 B1 | 3/2004 | Hirt et al. |
| 6,726,721 B2 | 4/2004 | Stoy et al. |
| 6,733,533 B1 | 5/2004 | Lozier |
| 6,734,000 B2 | 5/2004 | Chin et al. |
| 6,740,118 B2 | 5/2004 | Eisermann et al. |
| 6,773,713 B2 | 8/2004 | Bonassar et al. |
| 6,783,546 B2 | 8/2004 | Zucherman et al. |
| 6,800,298 B1 | 10/2004 | Burdick et al. |
| 6,802,863 B2 | 10/2004 | Lawson et al. |
| 6,827,743 B2 | 12/2004 | Eisermann et al. |

| Patent No. | Date | Name |
|---|---|---|
| 6,840,960 B2 | 1/2005 | Bubb |
| 6,849,092 B2 | 2/2005 | Van Dyke et al. |
| 6,855,743 B1 | 2/2005 | Gvozdic |
| 6,875,232 B2 | 4/2005 | Nigam |
| 6,875,386 B1 | 4/2005 | Ward et al. |
| 6,875,442 B2 | 4/2005 | Holy et al. |
| 6,878,384 B2 | 4/2005 | Cruise et al. |
| 6,881,228 B2 | 4/2005 | Zdeblick et al. |
| 6,893,463 B2 | 5/2005 | Fell et al. |
| 6,893,466 B2 | 5/2005 | Trieu |
| 6,923,811 B1 | 8/2005 | Carl et al. |
| 6,960,617 B2 | 11/2005 | Omidian et al. |
| 6,982,298 B2 | 1/2006 | Calabro et al. |
| 6,993,406 B1 | 1/2006 | Cesarano, III et al. |
| 7,008,635 B1 | 3/2006 | Coury et al. |
| 7,012,034 B2 | 3/2006 | Heide et al. |
| 7,022,522 B2 | 4/2006 | Guan et al. |
| 7,048,766 B2 | 5/2006 | Ferree |
| 7,052,515 B2 | 5/2006 | Simonson |
| 7,060,097 B2 | 6/2006 | Fraser et al. |
| 7,066,958 B2 | 6/2006 | Ferree |
| 7,066,960 B1 | 6/2006 | Dickman |
| 7,083,649 B2 | 8/2006 | Zucherman et al. |
| 7,091,191 B2 | 8/2006 | Laredo et al. |
| 7,156,877 B2 | 1/2007 | Lotz et al. |
| 7,186,419 B2 | 3/2007 | Petersen |
| 7,201,774 B2 | 4/2007 | Ferree |
| 7,201,776 B2 | 4/2007 | Ferree et al. |
| 7,214,245 B1 | 5/2007 | Marcolongo et al. |
| 7,217,294 B2 | 5/2007 | Kusanagi et al. |
| 7,235,592 B2 | 6/2007 | Muratoglu et al. |
| 7,250,060 B2 | 7/2007 | Trieu |
| 7,258,692 B2 | 8/2007 | Thelen et al. |
| 7,264,634 B2 | 9/2007 | Schmieding |
| 7,282,165 B2 | 10/2007 | Williams, III et al. |
| 7,291,169 B2 | 11/2007 | Hodorek |
| 7,316,919 B2 | 1/2008 | Childs et al. |
| 7,332,117 B2 | 2/2008 | Higham et al. |
| 7,357,798 B2 | 4/2008 | Sharps et al. |
| 7,377,942 B2 | 5/2008 | Berry |
| 7,682,540 B2 | 3/2010 | Boyan et al. |
| 7,828,853 B2 | 11/2010 | Ek et al. |
| 7,910,124 B2 | 3/2011 | Boyan et al. |
| 8,002,830 B2 | 8/2011 | Boyan et al. |
| 8,142,808 B2 | 3/2012 | Boyan et al. |
| 2001/0029399 A1 | 10/2001 | Ku |
| 2001/0038831 A1 | 11/2001 | Park et al. |
| 2001/0046488 A1 | 11/2001 | Vandenburgh et al. |
| 2002/0026244 A1 | 2/2002 | Trieu |
| 2002/0031500 A1 | 3/2002 | MacLaughlin et al. |
| 2002/0034646 A1 | 3/2002 | Canham |
| 2002/0072116 A1 | 6/2002 | Bhatia et al. |
| 2002/0140137 A1 | 10/2002 | Sapieszko et al. |
| 2002/0173855 A1 | 11/2002 | Mansmann |
| 2002/0183845 A1 | 12/2002 | Mansmann |
| 2002/0183848 A1 | 12/2002 | Ray et al. |
| 2002/0187182 A1 | 12/2002 | Kramer et al. |
| 2003/0008395 A1 | 1/2003 | Holy et al. |
| 2003/0008396 A1 | 1/2003 | Ku |
| 2003/0021823 A1 | 1/2003 | Landers et al. |
| 2003/0055505 A1 | 3/2003 | Sicotte et al. |
| 2003/0059463 A1 | 3/2003 | Lahtinen |
| 2003/0082808 A1 | 5/2003 | Guan et al. |
| 2003/0175656 A1 | 9/2003 | Livne et al. |
| 2003/0176922 A1 | 9/2003 | Lawson et al. |
| 2003/0199984 A1 | 10/2003 | Trieu |
| 2003/0220695 A1 | 11/2003 | Sevrain |
| 2003/0233150 A1 | 12/2003 | Bourne et al. |
| 2004/0010048 A1 | 1/2004 | Evans et al. |
| 2004/0024465 A1 | 2/2004 | Lambrecht et al. |
| 2004/0044412 A1 | 3/2004 | Lambrecht et al. |
| 2004/0052867 A1 | 3/2004 | Canham |
| 2004/0059425 A1 | 3/2004 | Schmieding |
| 2004/0063200 A1 | 4/2004 | Chaikof et al. |
| 2004/0064195 A1 | 4/2004 | Herr |
| 2004/0073312 A1 | 4/2004 | Eisermann et al. |
| 2004/0092653 A1 | 5/2004 | Ruberti et al. |
| 2004/0117022 A1 | 6/2004 | Marnay et al. |
| 2004/0143327 A1 | 7/2004 | Ku |
| 2004/0143329 A1 | 7/2004 | Ku |
| 2004/0143333 A1 | 7/2004 | Bain et al. |
| 2004/0147016 A1 | 7/2004 | Rowley et al. |
| 2004/0171143 A1 | 9/2004 | Chin et al. |
| 2004/0172135 A1 | 9/2004 | Mitchell |
| 2004/0220296 A1 | 11/2004 | Lowman et al. |
| 2004/0220669 A1 | 11/2004 | Studer |
| 2004/0220670 A1 | 11/2004 | Eisermann et al. |
| 2004/0249465 A1 | 12/2004 | Ferree |
| 2005/0037052 A1 | 2/2005 | Udipi et al. |
| 2005/0043733 A1 | 2/2005 | Eisermann et al. |
| 2005/0043802 A1 | 2/2005 | Eisermann et al. |
| 2005/0049706 A1 | 3/2005 | Brodke et al. |
| 2005/0055094 A1 | 3/2005 | Kuslich |
| 2005/0055099 A1 | 3/2005 | Ku |
| 2005/0071003 A1 | 3/2005 | Ku |
| 2005/0074877 A1 | 4/2005 | Mao |
| 2005/0079200 A1 | 4/2005 | Rathenow et al. |
| 2005/0090901 A1 | 4/2005 | Studer |
| 2005/0096744 A1 | 5/2005 | Trieu et al. |
| 2005/0106255 A1 | 5/2005 | Ku |
| 2005/0137677 A1 | 6/2005 | Rush |
| 2005/0137707 A1 | 6/2005 | Malek |
| 2005/0143826 A1 | 6/2005 | Zucherman et al. |
| 2005/0149196 A1 | 7/2005 | Zucherman et al. |
| 2005/0154462 A1 | 7/2005 | Zucherman et al. |
| 2005/0154463 A1 | 7/2005 | Trieu |
| 2005/0169963 A1 | 8/2005 | Van Dyke et al. |
| 2005/0171608 A1 | 8/2005 | Peterman et al. |
| 2005/0177238 A1 | 8/2005 | Khandkar et al. |
| 2005/0196452 A1 | 9/2005 | Boyan et al. |
| 2005/0209704 A1 | 9/2005 | Maspero et al. |
| 2005/0216087 A1 | 9/2005 | Zucherman et al. |
| 2005/0228500 A1 | 10/2005 | Kim et al. |
| 2005/0233454 A1 | 10/2005 | Nies et al. |
| 2005/0244449 A1 | 11/2005 | Sayer et al. |
| 2005/0260178 A1 | 11/2005 | Vandenburgh et al. |
| 2005/0261682 A1 | 11/2005 | Ferree |
| 2005/0273176 A1 | 12/2005 | Ely et al. |
| 2005/0273178 A1 | 12/2005 | Boyan et al. |
| 2005/0277921 A1 | 12/2005 | Eisermann et al. |
| 2005/0278025 A1 | 12/2005 | Ku et al. |
| 2005/0287187 A1 | 12/2005 | Mansmann |
| 2006/0002890 A1 | 1/2006 | Hersel et al. |
| 2006/0052874 A1 | 3/2006 | Johnson et al. |
| 2006/0052875 A1 | 3/2006 | Bernero et al. |
| 2006/0052878 A1 | 3/2006 | Schmieding |
| 2006/0058413 A1 | 3/2006 | Leistner et al. |
| 2006/0064172 A1 | 3/2006 | Trieu |
| 2006/0064173 A1 | 3/2006 | Guederian |
| 2006/0083728 A1 | 4/2006 | Kusanagi et al. |
| 2006/0100304 A1 | 5/2006 | Vresilovic et al. |
| 2006/0121609 A1 | 6/2006 | Yannas et al. |
| 2006/0122706 A1 | 6/2006 | Lo |
| 2006/0136064 A1 | 6/2006 | Sherman |
| 2006/0136065 A1 | 6/2006 | Gontarz et al. |
| 2006/0200250 A1 | 9/2006 | Ku |
| 2006/0206209 A1 | 9/2006 | Cragg et al. |
| 2006/0224244 A1 | 10/2006 | Thomas et al. |
| 2006/0229721 A1 | 10/2006 | Ku |
| 2006/0235541 A1 | 10/2006 | Hodorek |
| 2006/0257560 A1 | 11/2006 | Barone et al. |
| 2006/0259144 A1 | 11/2006 | Trieu |
| 2006/0282165 A1 | 12/2006 | Pisharodi |
| 2006/0282166 A1 | 12/2006 | Molz et al. |
| 2006/0287730 A1 | 12/2006 | Segal et al. |
| 2006/0293561 A1 | 12/2006 | Abay |
| 2006/0293751 A1 | 12/2006 | Lotz et al. |
| 2007/0010889 A1 | 1/2007 | Francis |
| 2007/0014867 A1 | 1/2007 | Kusanagi et al. |
| 2007/0032873 A1 | 2/2007 | Pisharodi |
| 2007/0038301 A1 | 2/2007 | Hudgins |
| 2007/0043441 A1 | 2/2007 | Pisharodi |
| 2007/0067036 A1 | 3/2007 | Hudgins et al. |
| 2007/0073402 A1 | 3/2007 | Vresilovic et al. |
| 2007/0093906 A1 | 4/2007 | Hudgins et al. |
| 2007/0106387 A1 | 5/2007 | Marcolongo et al. |
| 2007/0116678 A1 | 5/2007 | Sung et al. |
| 2007/0118218 A1 | 5/2007 | Hooper |

| | | | | | | |
|---|---|---|---|---|---|---|
| 2007/0118225 A1 | 5/2007 | Hestad et al. | | JP | 2005-199054 | 7/2005 |
| 2007/0134333 A1 | 6/2007 | Thomas et al. | | JP | 07247365 | 9/2005 |
| 2007/0135922 A1 | 6/2007 | Trieu | | JP | 2006-101893 | 4/2006 |
| 2007/0142326 A1 | 6/2007 | Shue | | WO | WO 90/07545 | 7/1990 |
| 2007/0162135 A1 | 7/2007 | Segal et al. | | WO | WO 90/07575 | 7/1990 |
| 2007/0164464 A1 | 7/2007 | Ku | | WO | WO 90/10018 | 9/1990 |
| 2007/0167541 A1 | 7/2007 | Ruberti et al. | | WO | WO 93/16664 | 9/1993 |
| 2007/0168039 A1 | 7/2007 | Trieu | | WO | WO 94/01483 | 1/1994 |
| 2007/0173951 A1 | 7/2007 | Wijlaars et al. | | WO | WO 95/25183 | 9/1995 |
| 2007/0179606 A1 | 8/2007 | Huyghe et al. | | WO | WO 97/06101 | 2/1997 |
| 2007/0179614 A1 | 8/2007 | Heinz et al. | | WO | WO 97/46178 | 12/1997 |
| 2007/0179615 A1 | 8/2007 | Heinz et al. | | WO | WO 98/02146 | 1/1998 |
| 2007/0179617 A1 | 8/2007 | Brown et al. | | WO | WO 98/50017 | 12/1998 |
| 2007/0179618 A1 | 8/2007 | Trieu et al. | | WO | WO 99/25391 | 5/1999 |
| 2007/0179620 A1 | 8/2007 | Seaton, Jr. et al. | | WO | WO 99/34845 | 7/1999 |
| 2007/0179621 A1 | 8/2007 | McClellan, III et al. | | WO | WO 00/30998 | 6/2000 |
| 2007/0179622 A1 | 8/2007 | Denoziere et al. | | WO | WO 00/42991 | 7/2000 |
| 2007/0196454 A1 | 8/2007 | Stockman et al. | | WO | WO 00/62829 | 10/2000 |
| 2007/0202074 A1 | 8/2007 | Shalaby | | WO | WO00/66191 | 11/2000 |
| 2007/0203095 A1 | 8/2007 | Sadozai et al. | | WO | WO 01/02033 | 1/2001 |
| 2007/0203580 A1 | 8/2007 | Yeh | | WO | WO 01/22902 | 4/2001 |
| 2007/0208426 A1 | 9/2007 | Trieu | | WO | WO 01/59160 | 8/2001 |
| 2007/0213718 A1 | 9/2007 | Trieu | | WO | WO 01/64030 | 9/2001 |
| 2007/0213822 A1 | 9/2007 | Trieu | | WO | WO 01/70436 | 9/2001 |
| 2007/0213823 A1 | 9/2007 | Trieu | | WO | WO 01/91822 | 12/2001 |
| 2007/0213824 A1 | 9/2007 | Trieu | | WO | WO 02/09647 | 2/2002 |
| 2007/0213825 A1 | 9/2007 | Thramann | | WO | WO 02/30480 | 4/2002 |
| 2007/0224238 A1 | 9/2007 | Mansmann et al. | | WO | WO 02/064182 | 8/2002 |
| 2007/0225823 A1 | 9/2007 | Hawkins et al. | | WO | WO 03/030787 | 4/2003 |
| 2007/0227547 A1 | 10/2007 | Trieu | | WO | WO 03/092760 | 11/2003 |
| 2007/0233259 A1 | 10/2007 | Muhanna et al. | | WO | WO 2004/060554 | 7/2004 |
| 2007/0265626 A1 | 11/2007 | Seme | | WO | WO 2004/101013 | 11/2004 |
| 2007/0270876 A1 | 11/2007 | Kuo et al. | | WO | WO 2005/077013 | 8/2005 |
| 2007/0270970 A1 | 11/2007 | Trieu | | WO | WO 2005/077304 | 8/2005 |
| 2007/0270971 A1 | 11/2007 | Trieu et al. | | WO | WO 2005/097006 | 10/2005 |
| 2007/0299540 A1 | 12/2007 | Ku | | WO | WO 2006/018531 | 2/2006 |
| 2008/0004707 A1 | 1/2008 | Cragg et al. | | WO | WO 2006/019634 | 2/2006 |
| 2008/0015697 A1 | 1/2008 | McLeod et al. | | WO | WO 2006/030054 | 3/2006 |
| 2008/0021563 A1 | 1/2008 | Chudzik | | WO | WO 2006/034365 | 3/2006 |
| 2008/0031962 A1 | 2/2008 | Boyan et al. | | | | |
| 2008/0045949 A1 | 2/2008 | Hunt et al. | | | | |
| 2008/0051889 A1 | 2/2008 | Hodorek | | | | |

OTHER PUBLICATIONS

Kwak, BK, et al., "Chitin-based Embolic Materials in the Renal Artery of Rabbits: Pathologic Evaluation of an Absorbable Particulate Agent", Radiology, 236:151-158 (2005).

Katta et al., "Friction and wear behavior of poly(vinyl alcohol)/poly(vinyl pyrrolidone) hydrogels for articular cartilage replacement," Journal of Biomedical Materials Research, vol. 83A, pp. 471-479 (2007).

Ma et al., "Friction Properties of novel PVP/PVA blend hydrogels as artificial cartilage," Journal of Biomedical Materials Research, vol. 93A, pp. 1016-1019 (2010).

Andrade et al., "Water as a Biomaterial," Trans. Am. Soc. Artif. Intern. Organs, 19:1 (1973).

Ariga et al., "Immobilization of Microorganisms with PVA Hardened by Iterative Freezing and Thawing," Journal of Fermentation Technology, 65(6): pp. 651-658 (1987).

Boyan et al., "Effect of Titanium Surface Characteristics on Chondrocytes and Osteoblasts in Vitro," Cells and Materials, vol. 5, No. 4, pp. 323-335 (1995).

Boyan et al., "Osteoblast-Mediated Mineral Deposition in Culture is Dependent on Surface Microtopography," Calcif. Tissue Int., 71:519-529 (2002).

Brunette, "The Effects of Implant Surface Topography on the Behavior of Cells," Int. J. Oral Maxillofac Implants, 3:231-246 (1988).

Chen et al., "Boundary layer infusion of heparin prevents thrombosis and reduces neointimal hyperplasia in venous polytetrafluoroethylene grafts without system anticoagulation," J. Vascular Surgery, 22:237-247 (1995).

Chu et al., "Polyvinyl Alcohol Cryogel: An Ideal Phantom Material for MR Studies of Arterial Elasticity," Magnetic Resonance in Medicine, v. 37, pp. 314-319 (1997).

Hickey et al., "Mesh size and diffusive characteristics of semicrystalline poly(vinyl alcohol) membranes prepared by freezing/thawing techniques," Journal of Membrane Science, 107(3), pp. 229-237 (1995).

| | | |
|---|---|---|
| 2008/0057128 A1 | 3/2008 | Li et al. |
| 2008/0075657 A1 | 3/2008 | Abrahams et al. |
| 2008/0077242 A1 | 3/2008 | Reo et al. |
| 2008/0077244 A1 | 3/2008 | Robinson |
| 2008/0097606 A1 | 4/2008 | Cragg et al. |
| 2008/0103599 A1 | 5/2008 | Kim et al. |
| 2008/0114367 A1 | 5/2008 | Meyer |
| 2008/0125870 A1 | 5/2008 | Carmichael et al. |
| 2008/0131425 A1 | 6/2008 | Garcia et al. |
| 2008/0145404 A1 | 6/2008 | Hill et al. |
| 2008/0166329 A1 | 7/2008 | Sung et al. |
| 2008/0279941 A1 | 11/2008 | Boyan et al. |
| 2008/0279943 A1 | 11/2008 | Boyan et al. |
| 2009/0182421 A1 | 7/2009 | Silvestrini et al. |
| 2009/0263446 A1 | 10/2009 | Boyan et al. |
| 2011/0040332 A1 | 2/2011 | Culbert et al. |
| 2011/0172771 A1 | 7/2011 | Boyan et al. |

FOREIGN PATENT DOCUMENTS

| | | |
|---|---|---|
| EP | 0222404 | 5/1987 |
| EP | 0346129 | 12/1989 |
| EP | 0505634 | 9/1992 |
| EP | 0410010 | 10/1993 |
| EP | 0411105 | 6/1995 |
| EP | 0845480 | 3/1998 |
| EP | 0919209 | 6/1999 |
| EP | 1287796 | 3/2003 |
| EP | 1030697 | 8/2003 |
| EP | 1344538 | 9/2003 |
| EP | 1584338 | 10/2005 |
| EP | 1482996 | 11/2005 |
| EP | 0222407 | 5/2007 |
| GB | 02056882 | 3/1981 |
| GB | 02128501 | 5/1984 |
| JP | 02-184580 | 7/1990 |
| JP | 04053843 | 2/1992 |
| JP | 11035732 | 9/1999 |

Hoffman et al., "Interactions of Blood and Blood Components at Hydrogel Interfaces," Ann. New York Acad. Sci., 283:372-382 (1977).

International Search Report for Application No. PCT/US2005/03899 mailed Jul. 15, 2008 (PCT/US2005/03899 is the corresponding PCT application of U.S. Appl. No. 11/053,410).

International Search Report for Application No. PCT/US2005/004045 mailed Jul. 15, 2005 (PCT/US2005/004045 is the corresponding PCT application of U.S. Appl. No. 11/053,409).

Kieswetter et al., "The Role of Implant Surface Characteristics in the Healing of Bone," Crit. Rev. Oral Biol. Med., 7(4):329-345 (1996).

Kieswetter et al., "Surface roughness modulates the local production of growth factors and cytokines by osteoblast-like MG-63 cells," Journal of Biomedical Materials Research, vol. 32, pp. 55-63 (1996).

Kohavi et al., "Markers of primary mineralization are correlated with bone-bonding ability of titanium or stainless steel in vivo," Clin. Oral. Impl. Res., 6:1-13 (1995).

Koutsopoulos et al., "Calcification of porcine and human cardiac valves: testing of various inhibitors for antimineralization," J. Mater. Sci. Mater. Med., 9:421-424 (1998).

Landolt et al., "Electrochemical micromachining, polishing and surface structuring of metals: fundamental aspects and new developments", Elsevier Science Ltd. (2003).

Lazzeri et al., "Physico-chemical and mechanical characterization of hydrogels of poly(vinyl alcohol) and hyaluronic acid," J. Mater. Sci. In Med., 5:852-867 (1994).

Liao et al., "Response of rat osteoblast-like cells to microstructured model surfaces in vitro," Biomaterials, 24, pp. 649-654 (2003).

Lozinsky et al., "Study of cryostructurization of polymer systems. VII. Structure formation under freezing of poly(vinyl alcohol) acqueous solutions," Colloid & Polymer Science, vol. 264, pp. 19-24 (1986).

Lozinsky et al., "Poly(vinyl alcohol) cryogels employed as matrices for cell immobilization. 2. Entrapped cells resemble porous fillers in their effects on the properties of PVA-cryogel carrier," Enzyme and Microbial Technology, vol. 20, No. 3, pp. 182-192 (1997).

Lozinsky et al., "Poly(vinyl alcohol) cryogels employed as matrices for cell immobilization. 3. Overview of recent research and developments," Enzyme and Microbial Technology, vol. 23, No. 3-4, pp. 227-242 (1998).

Lozinsky et al., "Study of Cryostructuration of Polymer Systems. XI. The Formation of PVA Cryogels by Freezing-Thawing the Polymer Aqueous Solutions Containing Additives of Some Polyols," Journal of Applied Polymer Science, vol. 58, pp. 171-177 (1995).

Lozinsky et al., "Study of Cryostructuration of Polymer Systems. XII. Poly(vinyl alcohol) Cryogels: Influence of Low-Molecular Electrolytes," Journal of Applied Polymer Science, vol. 61, pp. 1991-1998 (1986).

Lusta et al., "Immobilization of fungus *Aspergillus* sp. By a novel cryogel technique for production of extracellular hydrolytic enzymes", Process Biochemistry, vol. 35, pp. 1177-1182 (2000).

Martin et al., "Effect of titanium surface roughness on proliferation, differentiation, and protein synthesis of human osteoblast-like cells (MG63)," Journal of Biomedical Materials Research, vol. 29, pp. 389-401 (1995).

Nagura et al., "Structure of poly(vinyl alcohol) hydrogel prepared by repeated freezing and melting," Polymer, 30:762-765 (1989).

Oka et al., "Development of an Artificial Articular Cartilage", Clinical Materials, vol. 6, pp. 361-381 (1990).

Ong et al., "Osteoblast Responses to BMP-2-Treated Titanium in Vitro," The International Journal of Oral & Maxillofacial Implants, vol. 12, No. 5, pp. 649-654 (1997).

Peppas et al., "Structure of Hydrogels by Freezing-Thawing Cyclic Processing," Bulletin of the American Physical Society, 36:582 (1991).

Peppas et al., "Ultrapure poly(vinyl alcohol) hydrogels with mucoadhesive drug delivery characteristics," European Journal of Pharmaceutics and Biopharmaceutics, 43(1): 51-58 (1997).

Peppas et al., "Reinforced uncrosslinked poly(vinyl alcohol) gels produced by cyclic freezing-thawing processes: a short review," Journal of Controlled Release, 16(3): 305-310 (1991).

Peppas et al., "Controlled release from poly(vinyl alcohol) gels prepared by freezing-thawing processes," Journal of Controlled Release, vol. 18, pp. 95-100 (1992).

Ratner et al., Biomaterials Science an Introduction to Materials in Medicine, Academic Press, pp. 52, 53, & 62 (1996).

Schwartz et al., "Underlying Mechanisms at the Bone-Biomaterial Interface," Journal of Cellular Biochemistry, 56:340-347 (1994).

Singh et al., "Polymeric Hydrogels: Preparation and Biomedical Applications," J. Sci. Ind. Res., 39:162 (1980).

Stauffer et al., "Poly(vinyl alcohol) hydrogels prepared by freezing-thawing cyclic processing," Polymer 33(1818):3932-3936 (1992).

Stewart, J.E. et al., "Protein release from PVA gels prepared by freezing and thawing techniques," Proc. Int. Symp. Controlled Release Bioact. Mater., $26^{th}$, 1004-1005 (1999).

Szczesna-Antezak et al., "*Bacillus subtilis* cells immobilised in PVA-cryogels," Biomolecular Engineering, vol. 17, pp. 55-63 (2001).

The American Heritage ® Science Dictionary [online], Houghton Mifflin Company, 2002 [retrieved on Jun. 3, 2008]. Retrieved from the internet: <URL: http://dictionary.reference.com/browse/pore>.

Watase et al., "Rheological and DSC Changes in Poly(vinyl alcohol) Gels Induced by Immersion in Water," Journal of Polymer Science, Polym. Phys. Ed, 23(9): 1803-1811 (1985).

Watase et al., "Thermal and rheological properties of poly(vinyl alcohol) hydrogels prepared by repeated cycles of freezing and thawing," Makromol. Chem., v. 189, pp. 871-880 (1988).

Wilcox et al., "Microstructure of Poly(vinyl alcohol) Hydrogels Produced by Freeze/Thaw Cycling," Journal of Polymer Sciences: Part B: Polymer Physics, vol. 37, pp. 3438-3454 (1999).

WordNet ® 3.0 [online], Princeton University, 2006 [retrieved on Aug. 6, 2008]. Retrieved from the Internet: <URL: http://dictionary.reference.com/browse/mesh>.

Yamaura et al., "Properties of Gels Obtained by Freezing/Thawing of Poly(vinyl Alcohol)/Water/Dimethyl Sulfoxide Solutions," J. Appl. Polymer Sci., 37:2709-2718 (1989).

Yokoyama et al., "Morphology and structure of highly elastic poly(vinyl alcohol) hydrogel prepared by repeated freezing-and-melting", Colloid & Polymer Science, vol. 264, No. 7, pp. 595-601 (1986).

Zheng-Qiu et al., "The development of artificial articular cartilage—PVA-hydrogel," Bio-Medical Materials and Engineering, vol. 8, pp. 75-81 (1998).

Hunt, Knee Simulation, Creep, and Friction Tests of Poly(Vinyl Alcohol) Hydrogels Manufactured Using Injection Molding and Solution Casting, Thesis for M.S., University of Notre Dame (Jul. 2006).

Kobayashi et al., "Characterization of a polyvinyl alcohol-hydrogel artificial articular cartilage prepared by injection molding," J. Biomater. Sci. Polymer Edn., 15(6): 741-751 (2003).

Nakashima et al., "Study on Wear Reduction Mechanisms of Artificial Cartilage by Synergistic Protein Boundary Film Formation," Japan Soc'y of Mech. Eng'r Int'l J., Series C, vol. 48, No. 4, pp. 555-561 (2005).

Ricciardi et al., "Structure and Properties of Poly(vinyl alcohol) Hydrogels Obtained by Freeze/Thaw Techniques," Macromol. Symp., 222: 49-63 (2005).

Kobayashi et al., "Development of an artificial meniscus using polyvinyl alcohol-hydrogel for early return to, and continuance of, athletic life in sportspersons with severe meniscus injury. I: mechanical evaluation." The Knee, 10 (2003); 47-51.

Top View

Front View

Section A-A

METHOD OF MAKING LOAD BEARING HYDROGEL IMPLANTS

CROSS REFERENCE TO RELATED APPLICATIONS

This application is a continuation of U.S. patent application Ser. No. 11/053,409, filed Feb. 7, 2005, which claims the benefit of U.S. Provisional Patent Application Ser. No. 60/542,389, filed Feb. 6, 2004, both of which are incorporated by reference herein in their entireties.

BACKGROUND OF THE INVENTION

1. Field of the Invention

The invention relates to spinal disc replacement devices, particularly devices which mimic native spinal discs, for implantation which is compatible with living tissue. The invention also relates to implants suitable for load-bearing surfaces in the repair of tissue, replacement or augmentation, and methods of using such. One embodiment of the invention relates to an implantable spinal disc prosthesis.

2. Background Art

Materials used in the construction of implantable medical devices must be nontoxic, nonantigenic, and noninflammatory. Hydrogels are a preferred type of polymeric material for implantable devices. Because of their high water content, analogous to living tissue, they are superior in biocompatibility to non-hydrous polymeric materials.

U.S. Pat. No. 5,981,826, issued to Ku et al., describes the preparation of polyvinyl alcohol hydrogels (PVA-H) by physically crosslinking an aqueous solution of polyvinyl alcohol (PVA) to produce a gel. The crosslinking is accomplished by subjecting the aqueous PVA solution to multiple cycles of freezing and thawing. One limitation of the prior art is that the hydrogels produced are relatively nonporous and the pore size and degree of porosity, that is the density of the pores within the hydrogel, cannot vary independently of the mechanical properties or stiffness of the hydrogel.

Methods for producing certain porous hydrogels also exist in the art. U.S. Pat. No. 6,268,405, issued to Yao et al., describes methods for creating porous PVA-Hs by including immiscible materials in the polymerization process. After the hydrogel is polymerized, the included immiscible materials are washed out of the hydrogel by an appropriate solvent, yielding pores which are broadly distributed throughout the hydrogel. Controlling the size and density of the pores is accomplished by varying the molecular weight of the immiscible materials. A disadvantage of Yao et al. is that the range of attainable pore sizes is limited. Moreover, the invention of Yao et al. is limited in that it can only produce hydrogels whose pores extend throughout the hydrogel. The pores in Yao et al. are intended to create vascularization of the hydrogel in soft or non-load bearing tissue. A further disadvantage of Yao et al. is that the pore sizes are broadly distributed about the average pore size.

Artificial discs intended for the replacement of a damaged intravertebral disc have been described. These are typically articulated devices comprising two rigid metal plates adhered to opposite ends of an elastomeric core. In use, the artificial disc is placed in the intervertebral space and the metal plates are secured to the surfaces of adjacent vertebrae. Various embodiments of artificial discs of this type are described in U.S. Pat. Nos. 5,674,296 and 6,156,067, issued to Bryan et al., U.S. Pat. No. 5,824,094, issued to Serhan et al., U.S. Pat. No. 6,402,785, issued to Zdeblick et al. More recent embodiments, e.g. U.S. Pat. No. 6,419,704, issued to Ferree and U.S. Pat. No. 6,482,234, issued to Weber et al., include descriptions of elastomeric cores that may be formed from materials with different elasticities to better mimic the native structure of spinal discs.

Artificial discs have also been described wherein the disc is comprised of a flexible urethane silicone blend core and two identical rigid surfaces on either side of the core. U.S. Pat. No. 6,607,558 to Kuras describes such a disc where nail like projections extend from the surface to fixate the disc between the vertebrae. Such a disc also possesses a different material for the end plates as for the elastic core.

The disadvantage of the artificial disc devices of the prior art are numerous. These prior art devices require the mechanical attachment of rigid artificial materials, such as titanium, directly to the bone with screws, staples, nails, cement, or other mechanical means. These rigid materials are only minimally compatible with natural, living bone and separation of the implant from the bone is often observed over long-term implantation. In addition, materials used in artificial discs of the prior art have physical and mechanical properties distinctly different from those of natural spinal discs and thus inadequately duplicate the desired properties of native spinal discs.

Vertebral fusion is still the most commonly performed procedure to treat debilitating pain associated with degenerative spinal disc disease or disc trauma, despite the fact that the procedure has many drawbacks. Vertebral fusion increases stress and strain on the discs adjacent to the fusion site, and it is now widely accepted that fusion is responsible for the accelerated degeneration of adjacent levels. Current multicomponent spinal disc prosthesis designs, elastomeric cores with metal plates on both the upper and lower surfaces, are susceptible to problems with interfacial bonding and wear. These designs have shown spontaneous device detachment due to retraction of bone tissue from the metal surface.

Bone ingrowth and attachment in the art has often required the use of bone promoting growth factors. For example, U.S. Pat. No. 5,108,436, issued to Chu et al., describes using a porous implant for use in load bearing bone replacement which is used in combination with an osteogenic factor such as TGF-$\beta$.

Biomedical devices which are implanted in or around bone often fail because of fibrinogen encapsulation of the implant instead of cellular attachment to the implant itself. This encapsulation is a defensive reaction attempting to minimize contact between the body and the implant and is considered a sign of implant incompatibility.

Moreover, the art of bone ingrowth onto implantable surface contains a multitude of examples relating to porous directed ingrowth where bone essentially grows into and around channels of the implant. For example, U.S. Pat. No. 4,911,720, issued to Collier et al., discusses the ingrowth of bone into interconnecting pores which essentially locks bone into place. This method is disadvantageous in that bone does not actually attach itself to the material, instead bone attaches to other bone around the implant. In the unfortunate event that an implant must be removed, this type of Collier ingrowth results in large amounts of disruption to the surrounding bone tissue.

SUMMARY OF THE INVENTION

The present invention describes a hydrogel for implantation into a load bearing space within the body. The hydrogel has a textured surface on it which is comprised of superficial surface pores. Stated differently, the pores on the surface of the hydrogel substrate do not extend throughout the hydrogel but instead remain within a region near the surface. The pores on this hydrogel substrate can have an average diameter of between 1 and 100 micrometers. Preferably the average diameter of surface pores on the hydrogel substrate is between 5 and 50 micrometers, and preferably between 10 and 30 micrometers. The superficial pores of this hydrogel substrate can vary in size by less than 50%, preferably less than 30%, and preferably less than 10%. The hydrogel substrate of the present invention can be made up of polyvinyl alcohol and can have a water content of at least 5% w/w of the overall hydrogel. The hydrogel substrate of the present invention could be used in any load bearing implantable device application including, but not limited to, a spinal disc replacement. The present invention when used as a spinal disc replacement can possess the surface pores in the proper configuration and be additionally comprised of multiple regions of varying elasticities. It is also possible that the regions of varying elasticities of the spinal disc replacement be comprised of multiple hydrogels as opposed to one hydrogel of varying elasticities.

The present invention also includes a method for making a hydrogel substrate with a textured surface for use in a load bearing biocompatible device. The hydrogel in liquid form is exposed to solid objects or to a mold which when polymerized or hardened results in a hydrogel with a textured surface. The solid objects used to impart the superficial pores may be made of polystyrene beads. Also, the solid objects used to impart the superficial pores may be grit, sand, silicon, silica, and ultra-fine particulate matter. The solid objects used to create the superficial pores can have a diameter of between 1 and 100 micrometers, preferably between 5 and 50 micrometers, and preferably between 10 and 30 micrometers. The solid objects used to create the superficial pores of this invention can be removed, for example, by use of an organic solvent or other washing means. This hydrogel substrate can be comprised of poly-vinyl alcohol possessing a water content of at least 5% w/w of the overall hydrogel.

DETAILED DESCRIPTION OF THE INVENTION

The present invention is drawn to an implantable hydrogel substrate comprising a hydrogel surface having a plurality of superficial pores thereon. The pores on this hydrogel substrate can have an average diameter of between 1 and 100 micrometers. Preferably the average diameter of surface pores on the this hydrogel substrate is between 5 and 50 micrometers, and preferably between 10 and 30 micrometers. The superficial pores of this hydrogel substrate can vary in size by less than 50%, preferably less than 30%, and preferably by less than 10%. The hydrogel substrate of the present invention can be made up of polyvinyl alcohol and can have a water content of at least 5% w/w of the overall hydrogel.

One embodiment of the present invention is an artificial disc for implantation into the spine comprising the hydrogel substrate described above. This artificial disc is a hydrogel possessing a plurality of regions having variable elasticity. Specifically, the disc is comprised of a surface region having a higher modulus of elasticity than an interior region. This disc can be prepared using multiple hydrogels with the elastic properties of the one disc with varying regions of elasticity.

The present invention also includes a method for making a hydrogel substrate comprising contacting solid objects with an aqueous hydrogel, allowing the hydrogel to polymerize and crosslink while the solid objects are at least partially immersed in the hydrogel, and removing those solid objects from the polymerized and crosslinked hydrogel to form superficial pores thereon. The solid objects used to impart the superficial pores may be polystyrene beads. Alternatively, the solid objects used to impart the superficial pores may be grit, sand, silicon, silica, and ultra-fine particulate matter. The solid objects used to create the superficial pores and therefore the pores themselves can have a diameter of between 1 and 100 micrometers, preferably between 5 and 50 micrometers, and preferably between 10 and 30 micrometers.

The solid objects used to create the superficial pores of this invention can be removed for example by use of an organic solvent or other washing means. This hydrogel substrate can be comprised of poly-vinyl alcohol possessing a water content of at least 5% w/w of the overall hydrogel.

Accordingly, the present invention is directed to an implantable hydrogel substrate product, a method of making that product, and a method of using that product which substantially improves upon the limitations existing in the art. To achieve these and other advantages in accordance with the purpose of the invention, as embodied and broadly described herein, the invention includes a load bearing biocompatible hydrogel for medical implantation that promotes bone attachment. The hydrogel substrate consists of a hydrogel surface component which has been optimized for implantation. This is accomplished through pores on the surface having a controlled range in distribution of size. The surface pores are superficial and do not extend throughout the hydrogel.

Hydrogels are materials whose state is between that of a solid and of a liquid. Gels consist of polymeric, i.e. long chain, molecules linked together to form a three-dimensional network and are embedded in a liquid medium. In the case of hydrogels, the liquid medium comprises water. The polymer backbone of hydrogels is formed by hydrophilic monomer units and may be neutral or ionic. Examples of neutral and hydrophilic monomer units are ethylene oxide, vinyl alcohol, (meth)acrylamide, N-alkylated (meth)acrylamides, N-methylol(meth)acrylamide, N-vinylamides, N-vinylformamide, N-vinylacetamide, N-vinyl-N-methylacetamide, N-vinyl-N-methylformamide, hydroxyalkyl (meth)acrylates such as hydroxyethylmethacrylate, vinylpyrrolidone, (meth)acrylic esters of polyethylene glycol monoallyl ethers, allyl ethers, of polyethylene glycols, and sugar units such as glucose or galactose. Examples of cationic hydrophilic monomer units are ethyleneimine (in the protonated form), diallyldimethylammonium chloride and trimethylammonium propylmethacrylamide chloride. Examples of anionic monomer units are (meth)acrylic acid, crotonic acid, maleic acid, fumaric acid, itaconic acid, 2-acrylamido-2-methylpropanesulfonic acid, vinylsulfonic acid, vinylphosphonic acid, 2-methacryloyloxyethanesulfonic acid, 4-vinylbenzenesulfonic acid, allylsulfonic acid, vinyltoluenesulfonic acid and vinylbenzenephosphonic acid.

From the example listing above, a hydrogel for use in the present invention may be selected based upon its biocompatibility and stability at various hydration states. For the purposes of the present invention, a suitable hydrogel will have a moisture content of at least 5% w/w of the overall hydrogel, preferably at least 10%, 15%, 20%, 25%, 30%, 35%, 40%, 50%, 60%, 70%, or 80% w/w of the overall hydrogel.

Initial events following implantation of a biomaterial in an orthotropic surgical site include rapid adsorption of serum constituents onto the implant surface. The first cells that are likely to come into contact with the surface are polymorphonuclear cells, platelets, monocytes, and macrophages. These cells release bioactive factors that promote mesenchyrnal cell migration to the wound site. In addition to these natural factors associated with wound healing, surgeons frequently use bone graft and bone graft substitutes to improve bone formation. Such materials include osteoinductive agents such as demineralized bone matrix and bone morphogenetic protein. If appropriate signals are present mesenchymal cells with an osteoprogenitor phenotype will continue to differentiate into osteoblasts; of these a subset will become osteocytes. Ultimately, the newly formed bone will be remodeled via osteoclastic resorption. The present invention also provides that well-known grafting agents may be incorporated into the hydrogel composition, which includes, but is not limited to growth factors, angiogenic agents, antibiotics, and the like.

Chemically modified or polar surfaces are generally known to be able to produce more reactive protein adsorption to the implant surface than unmodified or non-polar surfaces. The increased reactivity of the proteins adsorbed onto the polar surface is thought to promote cellular adhesion to that surface. Therefore, the invention provides that the hydrogel composition can possess chemically modified or polar surfaces.

In general, many materials are well-tolerated in bone, but the success of long-term or chronic implantation often depends on the intimacy of the interface between the material surface and the bone. Microarchitecture of the surface is an important determinant of cell response. It has been observed that osteoblast phenotypic expression is surface-dependent. As described herein, specific surface characteristics enhance osteoblast differentiation while permitting proliferation, leading to optimal cell response to the implantation.

The mechanical properties of the material must be appropriate for the application. When the mechanical properties of the material are similar to the mechanical properties of the tissue adjacent to the implant, tissue tolerance of the artificial material is enhanced. Polymeric and elastomeric biomaterials can be fabricated with a wide range of mechanical properties, making them suitable for many applications as implantable devices. Because of their high water content, similar to that of living tissue, hydrogels are superior in biocompatibility to non-hydrous polymeric materials. Poly-vinyl alcohol (PVA) is an example of a polymer that can be used to form hydrogels, and has been studied extensively IL for its potential in biomedical applications. Poly-vinyl alcohol hydrogels (PVA-Hs) are biologically well tolerated and compatible with living cartilage tissue.

PVA-Hs can be produced from solution via repeated freezing and thawing cycles that increase the order of the microcrystalline regions, changing the dissolution properties, mesh size, and diffusion properties of the polymer. Also, PVA-Hs can be produced from solution via a slow and sustained transition through the freezing point of the solution. The mechanical properties of PVA-Hs can be varied over a wide range, and stable PVA gels can easily be produced to have an elastic modulus ranging from a few MPa, such as articular cartilage, to about 50 MPa, such as the stiffest portion of the annulus of spinal discs.

Increasing the porosity of a hydrogel substrate produces decreased mechanical strength. When porous hydrogels are used to provide the requisite surface of the present invention, it is advantageous that the porosity not extend throughout the hydrogel, but be limited to a relatively shallow depth below the surface. The thickness of the porous portion of the hydrogel is preferably less than 1 millimeter, less than 500 micrometers, and most preferable less than or equal to 200 micrometers.

The hydrogel substrates of the present invention can be used for implantation into any part of the body. One embodiment of this invention is an artificial intervertebral disc, comprising one or more hydrogels shaped substantially similarly to a natural inteverebral disc. The upper and lower surfaces of the hydrogel, or assembly of hydrogels, are constructed to have a rugose or textured surface with a defined porosity. That porosity depends primarily upon the size of a solid object used to create the surface texture. The surface texture is created by the distribution of pores that do not continue throughout the hydrogel, or, in other words, the pores are superficial. The size of the pores can be from 2 to 100 micrometers, preferably from 5 to 50 micrometers, and preferably, from 10 to 30 micrometers.

The porosity of the hydrogel surface embodied in this invention may be realized in a variety of ways. Molds may be constructed with patterning on the appropriate surfaces of the cavities in the mold. Alternatively, the porosity may be produced by abrasion of a smooth hydrogel surface after molding. Abrading the surface with grit will result in a surface textured such as desired in this invention. Techniques for applying and using abrasives are well known to those of skill in the art.

One technique for producing the surface roughness of artificial discs of this invention involves providing solid objects having the size and shape of the required surface rugosity and then using these solid objects as a template for the construction of a mold. Alternatively, these solid objects may be embedded in the hydrogels of the present invention during the molding process and removed afterwards. Removal of the solid objects leaves behind on the surface of the hydrogel pores, cavities, and other invaginations required for the texture of the surface to be obtained.

One example of a material that can be used as solid objects to impart the surface texture on the hydrogels of the present invention is polystyrene. Polystyrene beads, commonly called latex beads, are commercially available in sizes ranging from 0.02 to 1000 micrometers, and can have a very narrow size distribution. Such a narrow size distribution is advantageous for applications requiring uniform surface roughness. For example, when using polystyrene beads with an average diameter of 20.3 μm an acceptable range for the distribution of bead size would be .+−.0.6 μm, preferably .+−.0.5 μm, and preferably .+−.0.4 μm. Polystyrene beads may be obtained having surface functional groups useful for covalent chemical attachment of various chemical entities to the surface of the beads. Polystyrene beads may also be obtained either crosslinked or uncrosslinked. The latter type of beads are insoluble in water, but freely soluble in many organic solvents. Thus, one method for removal of the beads after the molding process is the dissolution of the beads in appropriate organic solvents.

The pores on the textured surface in this embodiment enable the surface to resemble native bone which has undergone osteoclastic resorption. When surface textured hydrogels are used to provide the requisite surface porosity, it is advantageous for the pores not to extend throughout the hydrogel, but instead be limited to a relatively shallow depth below the textured surface. The thickness of the porous portion of the hydrogel surface is preferably less than 1 millimeter, preferably less than or equal to 500 micrometers, and preferably less than or equal to about 200 micrometers.

The hydrogels of the present invention may contain bioactive factors to further stimulate cell growth or differentiation.

These factors, for instance attachment peptides, such as RGD containing peptides, and growth factors such as bone morphogenic proteins, insulin-like growth factor, platelet derived growth factor, fibroblast growth factor, cartilage-derived growth factor, transforming growth factor-beta, and parathyroid hormone related peptide, as well as other regulatory chemicals such as statins, prostaglandins, and mineral ions well-known in the art. These factors may be included in the hydrogels of this invention singly or in combination, and they may be included with or without binding proteins.

The hydrogels of the present invention may also contain bone or cartilage forming cells (osteoblasts or chondrocytes) or precursor cells to bone and cartilage forming cells such as mesenchymal stem cells or osteoprogenitor cells. These precursor cells have the capacity to differentiate into bone and/or cartilage forming cells. Cells may be included in the hydrogels of the present invention alone or in combination with bioactive factors to further stimulate cell growth or differentiation.

Natural intervertebral discs have a tough outer fibrocartilaginous ring called the annulus fibrosus and a soft, inner, highly elastic structure called the nucleus pulposus. The artificial discs of the present invention may contain an inner core constructed to mimic the physical and mechanical properties of the natural nucleus pulposus, surrounded by an annular region constructed to mimic the physical and mechanical properties of the natural annulus fibrosus.

In one embodiment, these regions comprise hydrogels whose water content, degree of polymerization, and degree of crosslinking are adjusted to produce the requisite physical and mechanical properties. The hydrogel comprising the inner core has a higher water content and/or a lower degree of polymerization and/or a lower degree of crosslinking to produce a relatively soft and elastic hydrogel. The hydrogel comprising the outer annular region has a lower water content and/or a higher degree of polymerization and/or crosslinking to produce a relatively hard outer hydrogel which mechanically is tough and stiff. The hydrogels comprising the upper and lower surfaces may substantially resemble the hydrogel comprising the annular region in terms of physical and mechanical properties, water content, and degrees of crosslinking and polymerization. The additional requirement, however, for the surfaces to be porous may allow or require a different combination of physical and mechanical properties in these hydrogels compared to the hydrogel comprising the outer annular region.

Figure 1:
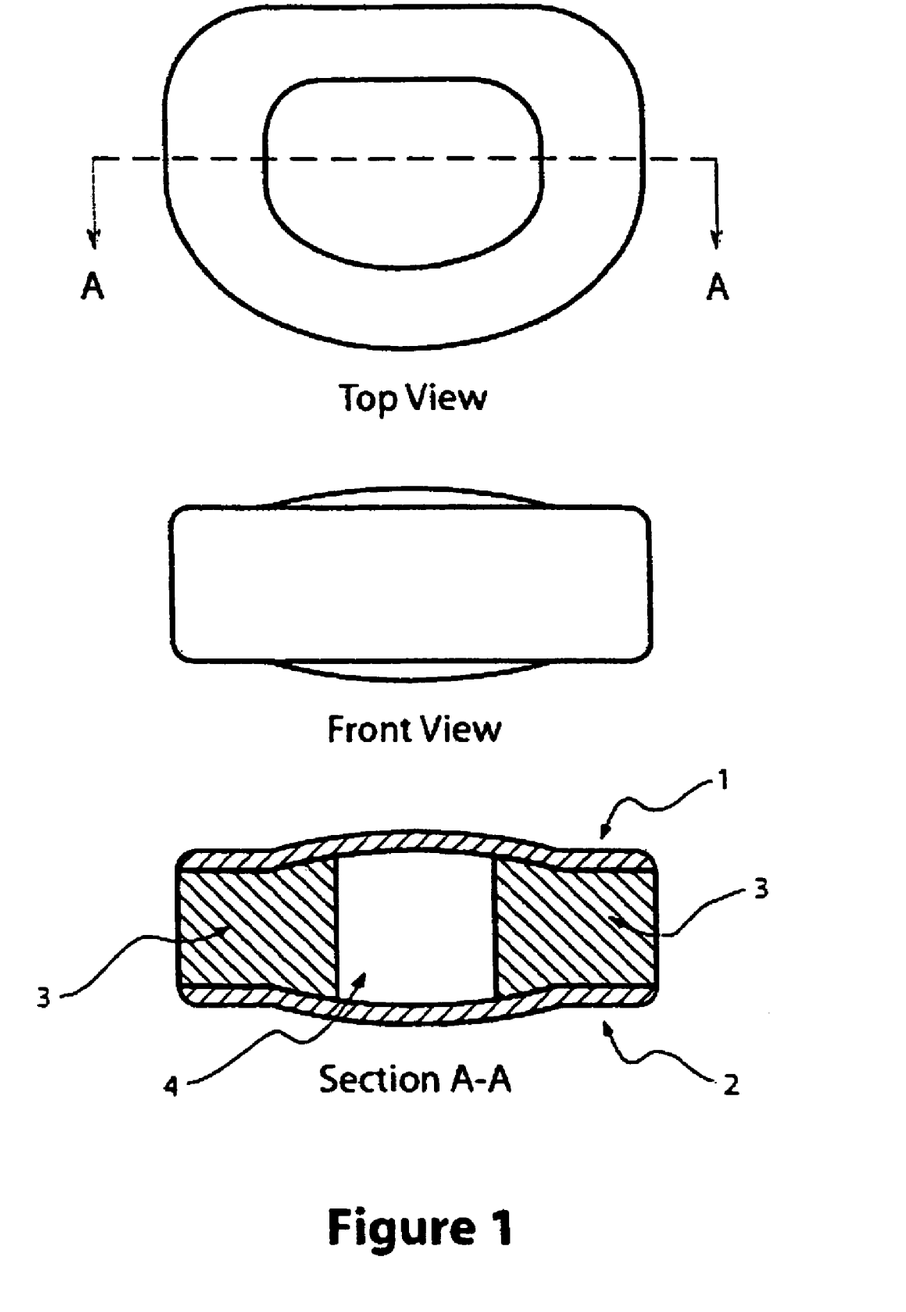
FIG. 1 is an elevation view of spinal disc replacement made in accordance with one embodiment of the present invention.

FIG. 1 shows a spinal disc replacement envisioned by the present invention. The spinal disc has an upper portion 1 and a lower portion 2. It is the hydrogel substrate surfaces of the upper portion 1 and lower portion 2 which possess the porous texture of the present invention. The upper portion 1 and lower portion 2 can be less elastic and more rigid than the inner region 4 which seeks to mimic the nucleus pulposus. Likewise, the spinal disc may have an intermediate region of elasticity 3 which further aids in the function of the spinal disc. The intermediate region of elasticity 3 may or may not differ from the elasticity of either the inner region 4 or the upper portion 1 or lower portion 2.

Figure 2:
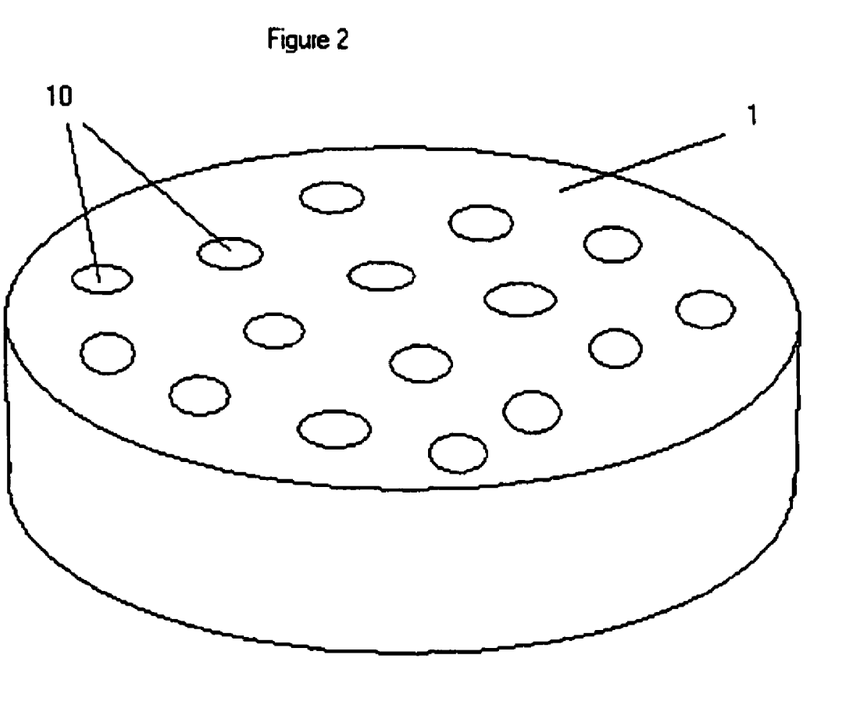
FIG. 2 is a schematic of a surface generated in accordance with one embodiment of the present invention.

FIG. 2 shows the upper portion 1 of the spinal disc of FIG. 1 possessing superficial surface pores 10 of the present invention. The sizing of these pores as described herein promotes differentiation of cells into desired tissues, such as bone or bone-like cells, and induces the attachment of those cells to the surface.

In one embodiment, the superficial pores can be created with solid polystyrene beads of 20.7 µm to 19.9 µm of average diameter suspended in the hydrogel solution, or coated on the appropriate surfaces of the mold prior to crosslinking of the hydrogel. After crosslinking, the polystyrene beads are removed by dissolving them in a solvent such as dimethyl formamide or its equivalent that does not dissolve the hydrogel. Such treatment produces porosity and surface roughness with dimensions approximately equal to the diameter of the polystyrene beads. The invaginations left behind after removal of the polystyrene beads contribute to the controlled surface texture desired in the present invention. The polystrene beads of this embodiment may also be adhered to a surface and used as a part of a mold, or as a template in the construction of a mold.

In another embodiment of this invention, the solid object used in the casting of a rough hydrogel surface is grit. Grit can be any solid object that is small with a narrow size distribution. Examples of grit include sand, silica particles, silicone particles, metal shot, etc. Those skilled in the art would recognize the need to match the grit used to the hydrogel along with the method of removing the grit leaving the rough or porous surface.

A silica grit of appropriate size can be used to impart the proper level of porosity on the surface of a hydrogel. As was seen with the polystyrene, the sand is placed in the bottom of a mold and the aqueous hydrogel is poured into the mold. The hydrogel is allowed to crosslink and polymerize and is then removed from the mold. The hydrogel is then washed to remove the grit leaving behind the invaginations and pores which make up the textured surface of the hydrogel implant. Grit may also be adhered to a surface and used as a part of a mold, or as a template in the construction of a mold.

In yet another embodiment of the present invention, the mold used in the formation of the hydrogel substrate can be any type of material around which the hydrogel forms. For example, the mold can be a series of beads, grit, filter screens, mesh, wires, glass tubing, and the equivalents of these materials or items. Once the hydrogel has been allowed to form around the mold element, the mold is removed from the hydrogel manually, chemically, or any other means which will allow the hydrogel to remain intact once the mold has been removed.

In yet another embodiment of the present invention, the hydrogel substrate can be a load bearing patch which can be used in the repair of partially or predominately damaged tissue. For example, the hydrogel substrate bearing the textured surface of the present invention can be relatively thin and small in diameter. That hydrogel substrate can then be placed where deteriorated, either acutely or chronically, cartilage was removed.

In yet another embodiment of the present invention, the hydrogel substrate can be assembled outside the body in a malleable form. The malleable form of the hydrogel substrate can then be placed in the intended area, be it a spinal disc replacement, knee cartilage replacement, shoulder bursa repair, or other use one skilled in the art would foresee. Once in the proper position, the malleable hydrogel substrate could be hardened or polymerized via photopolymerization. Radiation curing or photopolymerization (photo-induced free radical polymerization) has become an important and useful technique for applying and curing coatings, inks and adhesives. Radiation-curable compositions typically comprise as essential components one or more radiation-curable monomers and a photoinitiator. The compositions are applied as a coating to various articles and surfaces and the monomers are polymerized to form a film by exposing the coating of the radiation-curable composition to radiation, typically ultraviolet (UV) or electron-beam radiation.

EXAMPLES

Example 1

Attachment of Polystyrene Objects to a Surface

To a suspension of carboxyl-modified polystyrene beads (20.3 µm.+−.0.43 µm diameter, Bangs Laboratories) in 20 nM MEW, pH 4.4 is added a 10-fold excess of water-soluble carbodiimide, 1-ethyl-3-(d-dimethyylaminopropyl) carbodiimide hydrochloride. After 15 minutes at room temperature, the beads are washed twice by centrifugation and suspension in 20 mM HEPES, pH 7.5 and then resuspended in the same buffer. The resulting suspension is added to the wells of a 24-well tissue culture plate made of polycarbonate, having an amino-modified surface (Nalge Nunc International). After 60 minutes at room temperature, the unreacted beads are decanted, and the wells are washed gently with deionized water. Microscopic analysis shows the bottom surface of the wells are covered with a monolayer of polystyrene beads at a density of approximately 50%.

The surface with attached polystyrene objects of the previous example may be used as a template to fabricate a mold for providing the desired porous surface of the hydrogels of the present invention. This may be accomplished by making a metallic replica of a surface comprising a plurality of polystyrene objects using sputtering and/or metal plating techniques and the like, all of which are well known to those of skill in the art. The metallic replica thus produced may be replicated again and reinforced with further metal or other components, again using methods well known to those skilled in the art. The result is a mold suitable for producing the surface texture of the hydrogels of the present invention.

The polystyrene objects of the foregoing example may also be included in the hydrogels of the present invention during the molding process. Subsequent removal of the polystyrene objects provides the controlled surface porosity provided for the hydrogels of the present invention. This is illustrated in the following example.

Example 2

Construction of a PVA-H with Surface Topography for Implantation as a Spinal Disc Prosthesis A two-part mold with inserts is used to produce the artificial disc depicted in FIG. 1. The upper and lower halves of the mold are first separated to mold the upper and lower surface regions of the disc. The surface of each corresponding upper and lower surface is created by suspending in the aqueous hydrogel the objects for creating the superficial pores. That suspension is then poured into the well of a mold at a depth no greater than the desired depth of the superficial pores. That layer of hydrogel is allowed to polymerize and crosslink. From that base layer creating the outermost layer of the corresponding surface, the remainder of the bulk of the hydrogel substrate can be built up by adding additional depth of aqueous hydrogel.

A 30% w/w poly(vinyl alcohol) solution is prepared by mixing poly(vinyl alcohol) polymer (124,000-186,000 Av. MW, 99+% saponification, Aldrich Chemical Company) in sterile, deionized water. The polymer is dissolved by heating the mixture in an autoclave at 120° C. for 30 minutes. To a portion of the viscous liquid solution is added 30% w/w of the polystyrene objects from Example 1. This is mixed until a uniform suspension is obtained. To each of the cavities in each half of the mold is added a sufficient amount of this suspension to coat the surfaces of the mold cavities to a thickness of 200 µm. Inserts are placed in each cavity to spread the suspension across the surfaces of the cavities and maintain the 200 µm thickness.

The two halves of the mold are then subjected to five cycles of freezing and thawing. In each cycle, the molds are placed in a freezer at about −20° C. for approximately 12 hours then removed from the freezer and placed at room temperature for approximately 12 hours. The inserts defining the first 200 µm thickness of the top portion of the upper surface and the bottom portion of the lower surface are removed from the molds, and an additional amount of the 30% poly(vinyl alcohol) solution (without polystyrene objects) is added to the mold cavities. The amount added is sufficient to increase the thickness of the top portion of the upper surface and the bottom portion of the lower surface to 1 mm. Inserts are placed in each cavity to spread the solution and maintain the 1 mm thickness.

The two halves of the mold are subjected to five additional cycles of freezing and thawing as above. The inserts defining the top portion of the upper surface and the bottom portion of the lower surface are removed from the molds, and annular inserts defining the shape of the core region are placed in the cavities of the lower half of the mold. A 20% w/w poly(vinyl alcohol) solution is prepared by mixing poly(vinyl alcohol) polymer (89,000-98,000 Av. MW 99+% saponification, Aldrich Chemical Company) in sterile, deionized water and dissolving as above. The solution is filled into the annular inserts and the mold is subjected to five additional cycles of freezing and thawing. The annular inserts are removed, the two halves of the mold are assembled and clamped together, and the areas of the mold corresponding the annular region are filled with 30% poly(vinyl alcohol) solution. The assembled mold is subjected to five more cycles of freezing and thawing. The molded artificial discs are removed from the mold and immersed in dimethyl formamide to dissolve the included polystyrene objects, the rinsed three times with deionized water.

The artificial disc produced by the forgoing example has a soft and elastic inner core while the outer annular region and upper and lower surfaces are relatively hard, tough, and stiff. The surface of the artificial disc is smooth, except on the top portion of the upper surface and the bottom portion of the lower surface where the removal of the polystyrene objects produces a rough or rugose surface with a roughness of 20 µm. When artificial discs made according to this procedure are implanted into the intervertebral spaces of disectomized rabbits, extensive bone growth onto the surface occurs within 3 weeks.

Although the invention has been described with reference to a particular preferred embodiment with its constituent parts, features and the like, these are not intended to exhaust all possible arrangements, mechanical and electrical equivalents, or features, and indeed many other modifications and variations will be ascertainable to those of skill in the art.

What is claimed is:

1. A method of making a hydrogel having a hydrogel surface, comprising:
    contacting solid objects with a liquid hydrogel;
    allowing the liquid hydrogel to polymerize and crosslink while the solid objects are at least partially immersed along a surface region of the hydrogel; and
    removing said solid objects from the polymerized and crosslinked hydrogel to form a plurality of superficial pores thereon;
    wherein said superficial pores are located at or near said hydrogel surface; and wherein said superficial pores do not extend throughout an entire depth of said hydrogel; and wherein the polymerized and crosslinked hydrogel is load bearing.

2. The method of claim 1, wherein the solid objects comprise polystyrene beads.

3. The method of claim 1, wherein the solid objects comprise a material selected from the group consisting of one or more of the following: grit, sand, silicon, silica, and ultra-fine particulate matter.

4. The method of claim 1, wherein the solid objects have an average diameter of between about 1 to 100 micrometers.

5. The method of claim 1, wherein the solid objects have an average diameter of between about 5 to 50 micrometers.

6. The method of claim 1, wherein the solid objects have an average diameter of between about 10 and 30 micrometers.

7. The method of claim 1, wherein the superficial pores are within about 1 millimeter of the hydrogel surface.

8. The method of claim 1, wherein the superficial pores are within about 200 micrometers of the hydrogel surface.

9. The method of claim 1, wherein the solid objects are removed from the hydrogel using an organic solvent or washing.

10. The method of claim 1, wherein the hydrogel comprises polyvinyl alcohol.

11. The method of claim 1, wherein the hydrogel comprises a moisture content of at least about 5% w/w of the hydrogel.

12. The method of claim 1, wherein the hydrogel comprises a moisture content of at least about 30% w/w of the hydrogel.

* * * * *